United States Patent [19]

Mazanec et al.

[11] Patent Number: 4,675,306
[45] Date of Patent: Jun. 23, 1987

[54] PREPARATION OF CATALYST FOR PRODUCING ALCOHOLS

[75] Inventors: Terry J. Mazanec, Solon; John G. Frye, Jr., Euclid, both of Ohio

[73] Assignee: The Standard Oil Company, Cleveland, Ohio

[21] Appl. No.: 483,962

[22] Filed: Apr. 11, 1983

[51] Int. Cl.$^4$ .................. B01J 23/10; B01J 23/26; B01J 23/44; B01J 23/72
[52] U.S. Cl. .................. 502/303; 502/304; 502/307; 502/313; 502/316; 502/318; 502/324; 502/329; 502/331; 502/343; 518/713
[58] Field of Search ............ 502/304, 307, 313, 316, 502/318, 329, 331, 343, 303, 324; 518/713

[56] References Cited

U.S. PATENT DOCUMENTS

| | | | |
|---|---|---|---|
| 3,840,471 | 10/1974 | Acres | 502/307 |
| 4,071,473 | 1/1978 | Atkinson et al. | 502/302 |
| 4,233,185 | 11/1980 | Knapton et al. | 502/304 |
| 4,287,095 | 9/1981 | Atkinson et al. | 502/177 |

*Primary Examiner*—W. J. Shine
*Attorney, Agent, or Firm*—L. W. Evans; D. J. Untener; R. F. Keller

[57] ABSTRACT

Catalysts useful for the preparation of alcohols from synthesis gas and containing at leat three metal or metal oxide components are prepared by partially oxidizing an intermetallic compound or alloy with a metal oxidizing agent whereby the agent is incorporated into the catalyst.

9 Claims, No Drawings

PREPARATION OF CATALYST FOR PRODUCING ALCOHOLS

BACKGROUND OF THE INVENTION

1. Field of the Invention

The present invention relates generally to a novel method of preparing catalysts. More specifically, this invention relates to a method for preparing metal or metal oxide catalysts and their use in the production of alcohols.

2. Description of Art

Metal or metal oxide catalysts have long been known to catalyze reactions for the production of oxygenated compounds such as alcohols, aldehydes, ketones and carboxylic acids. It has also been recognized that it is usually desirable to obtain catalysts with the largest active surface area practicable and a number of standard techniques have been developed for this purpose. For example, impregnations, precipitations and ion-exchanges have been used to obtain high surface area metal or metal oxide containing catalysts.

Intermetallic catalysts having high surface areas are also known. These catalysts have been shown to be useful in hydrogenation reactions such as the formation of methane from synthesis gas and catalytic oxidation reactions such as the conversion of ammonia to oxides of nitrogen.

U.S. Pat. Nos. 4,256,653 and 4,071,473 disclose the preparation of transition metal catalysts for use in hydrogenation reactions. These catalysts are formed by reacting an alloy with a reactive gas to oxidize one of the alloy components while leaving the other component in a metallic state.

The present invention is a novel method for preparing catalysts containing metal or metal oxide components for use in producing alcohols by the partial oxidation of an intermetallic compound or alloy with a metal oxidizing agent which is incorporated into the catalyst as an active catalytic component. This novel method of catalyst preparation results in high surface area catalysts which are highly active for the production of alcohols. Further, catalysts can be prepared by the inventive method which cannot be prepared by conventional techniques.

SUMMARY OF THE INVENTION

According to this invention, catalysts containing at least three metal or metal oxide components are prepared by a method comprising partially oxidizing an intermetallic compound containing two or more metals with a metal oxidizing agent whereby the agent is incorporated into the catalyst.

These catalysts are useful for the production of alcohols from carbon monoxide and hydrogen.

DETAILED DESCRIPTION OF THE INVENTION

Catalyst Preparation

The catalysts of the present invention are prepared by the reaction of an intermetallic compound or alloy of two or more metals with a metal oxidizing agent which is preferably suspended or dispersed in solution. The final catalyst will contain at least three metal or metal oxide components and can be prepared in the absence of an oxidizing gas.

The intermetallic compounds or alloys contain at least two components which include the rare-earth elements such as the lanthanides or actinides and the transition metals such as Groups VIB, VIIB, VIIIB, IB and IIB of the Periodic Table. Preferably, the intermetallic compounds or alloys contain at least one metal selected from La, Th, Ce, U, Cu, Rh, Ru, Ir, Fe, Co, Pd, Pt, Zn and Cr. More preferably, the intermetallic compounds or alloys contain at least one metal selected from Th, Ce, Cu, Zn and Cr and most preferably contain copper. The ratio of metals in the intermetallic compound or alloy is not critical and a broad range of two or more components can be used to produce useful catalysts. Preferably, these compounds will contain more than 10 percent by weight Th, Ce, Cu, Zn or Cr and more preferably contain from about 20 to about 90 percent by weight Th, Ce, Cu, Zn or Cr.

Intermetallic compounds are known to those skilled in the art and characteristically exhibit a crystalline structure in which the metals are in stoichiometric amounts. These compounds are further detailed in *The Rare Earth Intermetallics*, by W. E. Wallace, Academic Press, 1973. Alloys generally differ from intermetallic compounds in that alloys usually do not exhibit a crystalline structure and the metals are not present in stoichiometric amounts. As used herein, the term intermetallic compound shall include metallic alloys.

The intermetallic compound can be prepared by any of the well known techniques for fusing two or more metal components. Arc melting or induction melting the metal components in an inert atmosphere, such as argon or helium, are satisfactory methods for forming these compounds. Once the compound is formed and cooled, preferably still under an inert atmosphere, it is then comminuted to a convenient particle size such as in the range from about 1 mm to 5 mm in diameter. Comminution may be accomplished using conventional crushing and grinding techniques.

The intermetallic compound is at least partially oxidized by a metal oxidizing agent which is thereby incorporated into the compound. The oxidizing metal agent can be selected from any of the transition metals known to exhibit oxidizing properties. Suitable metal oxidizing agents include but are not limited to Zn, Cr, Co, Mn, Ce, V, Pd, Cu, Ag, Fe, U, Rh, Ru, Os, Ir, Ni, and Th. Preferably, the metal oxidizing agent is Zn, Cr, Ce, or Pd.

The intermetallic compounds are oxidized by exposure to the metal oxidizing agent. Preferably, the intermetallic compound is placed in a solvent containing salts of the oxidizing metal agent and reacted although other techniques for oxidizing the intermetallic compound with the metal oxidizing agent can be employed. The solvent can be aqueous or organic such as alcohols, ethers, hydrocarbons or a combination thereof. Water has been found to be a suitable solvent and is preferably heated to temperatures sufficient to dissolve the salt of the metal oxidizing agent. Generally, the reaction mixture is heated to temperatures above about 20° C., and preferably between about 60° C. and about 100° C. for the reaction to proceed. Typically, the reaction is completed after 1 to 4 hours while stirring.

Once the reaction has completed, the solid precipitate is separated from the solution by standard techniques such as filtration. The precipitate or catalyst should be dried at a convenient temperature, for example 120° C. Optionally, the catalyst is then calcined for a time and at a temperature sufficient to drive out the remaining water in the precipitate and to cause cross-linking of and decompose the decomposable ions remaining in the precipitate, such as nitrates and carbonates. Temperatures from about 250° to about 500° C., preferably about 350° to about 450° C. for periods of several minutes to about 5 hours have been found sufficient for this purpose.

Since the catalyst of the present invention is generally used in a reducing atmosphere, it is preferable to reduce the catalyst prior to use. Pre-reduction of the catalyst, however, is not necessary since the catalyst will automatically undergo reduction to an equilibrium value in use, although the activity of the catalyst may not be as great as when a proper reduction procedure is carried out prior to use.

It is preferable to carry out a controlled reduction of the calcined precipitate in the following manner, although any other technique can also be employed. The calcined precipitate is heated under reducing atmosphere to a temperature of about 100° C. Next, the calcined precipitate is slowly heated over a period of about 2 to about 3 hours to a temperature of 150° C. The temperature is then slowly heated to the reaction temperature, such as 250° C., over a period of about 1 to about 2 hours. Upon reaching the reaction temperature, the temperature is held for about 1 hour to obtain the proper reduction of the metal. The catalyst is now ready to receive reactant.

The controlled reduction of the catalyst is used to control the run-away exotherms exhibited with rapid heating which tend to over reduce the metals. Although not intending to be bound to theory, it is believed that a controlled reduction only partially reduces the metals making the catalyst more catalytically active. Another useful technique for effecting controlled reductions is to slowly increase the amount of reducing gas used during reduction until the proper reduction is achieved.

The catalyst of the present invention can be used alone or supported on various inert supports such as silica, silica-alumina, alumina, mullite, zeolites, layered clays and the like. These support materials are preferably low surface area supports and can be added to the catalyst during the preparation (during oxidation) or after the preparation of the catalyst by conventional techniques. The intermetallic compound can also be supported on various inert supports prior to oxidation with the metal oxidizing agent.

A preferred mode of using the alcohol catalysts of this invention is accomplished by coating the catalyst material on an inert material using known techniques. Coating materials, such as the support materials mentioned above, can be physically mixed with the catalyst in a proper solvent and dried. Coating techniques are more fully disclosed in U.S. Pat. No. 4,077,912 which is hereby incorporated by reference.

Reaction

The material being reacted in accordance with the present invention to form alcohols is preferably synthesis gas. As well known, synthesis gas is composed basically of a mixture of hydrogen and carbon monoxide in which the $H_2/CO$ ratio is from 0.1/1 to 10/1, more normally from about 0.3/1 to about 3/1. Synthesis gas is normally derived by heating coke in the presence of air and then steamed. Alternatively, it can also be produced by heating coal, natural gas or petroleum hydrocarbons and is sometimes referred to as "water gas". Synthesis gas normally contains a very low amount of sulfur compounds and may contain small amounts of carbon dioxide, nitrogen and other trace gases.

Although synthesis gas is a preferred reactant, any other gas composed primarily of hydrogen and carbon monoxide and having a $H_2/CO$ ratio of about 0.1/1 to about 10/1 can be employed. Preferably, the $H_2/CO$ ratio is from about 0.5/1 to about 3/1 for the production of alcohols. The gaseous reactants should contain minimal amounts of sulfur compounds, since it has been known that sulfur may poison metal catalysts.

The catalyst of the present invention is contacted with a gaseous reactant in a suitable reactor. The reaction can be carried out either in a fluid-bed mode or a fixed-bed mode, as examplified herein, continuously or in batch operation.

The contact time of the reactants with the catalyst is not critical but is generally below about 200 seconds and preferably between about 10 and about 125 seconds.

The reaction pressure should normally be between about 500 and about 1,500 psi and is preferably between about 750 and about 1,000 psi. Although there is no real upper limit to the reaction pressure, pressures higher than 1,500 psi are normally not employed because of the high expense involved. Also, pressures as low as 250 psi can be employed although it is preferable to operate at least about 500 psi.

The reaction temperature should be maintained between about 200° and about 425° C., preferably about 250° and about 350° C., and most preferably about 280° and about 330° C. The reaction temperature, like the reaction pressure, is not particularly critical, although a marked decrease in conversion rates may be obtained if temperatures and pressures are lower than about 200° C. and about 250 psi. Moreover, lower temperatures such as below 330° C. favor the production of low molecular weight alcohols, particularly methanol.

The inventive catalysts can be used to produce alcohol mixtures comprising $C_1$ to $C_{20}$ saturated or unsaturated alcohols. Preferably, the alcohol mixtures will be saturated $C_1$ to $C_4$ and most preferably comprise predominantly methanol. However, these catalysts can also produce other oxygenated compounds, such as aldehydes, ketones, carboxylic acids and like.

SPECIFIC EMBODIMENTS

Catalyst Preparation

EXAMPLE 1

A 70.15 gram sample of $Cu_2Th$ obtained commercially from Cerac, Inc., Milwaukee, Wis., and ground to a fine powder (about 30–80 mesh) was added slowly over a course of about 1 hour to a stirred solution of 4.52 grams of $Pd(NO_3)_2$ in about 600 ml. of distilled water at about 70° C. Stirring was continued for an additional 2 hours at about 75° C. after which the precipitate was separated by filtration, washed with water and dried at 125° C. for 4 hours. The solid material was then calcined in air at 400° C. for 4 hours.

The above catalyst was coated on alundum according to the following procedure. Between 20 and 30 grams of alundum (10–30 mesh) and 10–12 grams of catalyst powder were mixed with about 2 grams of water. The mixture is thoroughly mixed in a ball mill for about 3 hours, and dried in air at 115° C. The coated catalyst is then used for the production of alcohols.

EXAMPLE 2

Example 2 was prepared in accordance with the procedure used in Example 1 except 3.70 gms. of $Ce(NO_3)_3$ was used in place of the $Pd(NO_3)_2$ and 29.86 gms. of $Cu_2Th$ was used.

EXAMPLE 3

Example 3 was prepared in accordance with the procedure used in Example 1 except 30.34 gms. of $Cu_2Th$ was used and the $Pd(NO_3)_2$ was replaced with 2.50 gms. of $Zn(NO_3)_2$.

EXAMPLE 4

Example 4 was prepared in accordance with the procedure of Example 1 except the intermetallic compound used was $Cu_2Ce$ (41.90 gms.) and the $Pd(NO_3)_2$ was replaced with 2.55 gms. of $Cr(NO_3)_3$.

EXAMPLE 5

Example 5 was prepared in accordance with the procedure of Example 4 except 29.37 gms. of $Cu_2Ce$ was used and the $Cr(NO_3)_3$ was replaced with 2.53 gms. of $Zn(NO_3)_2$.

Production of Alcohols

A 20.0 cc. sample of the catalysts of Examples 1–5 were reduced in situ by placing the catalyst sample into a stainless steel, fixed bed reactor. The catalyst was contacted with nitrogen and hydrogen at a flow rate of 1.5 SLPM. and 0.3 SLPM., respectively, at 1 atmosphere. The reactor was then heated from room temperature to 100° C. over a period of 1 hour, raised slowly to 150° C. over a period of 2 hours, raised again to 250° C. over a period of 1 hour and maintained at 250° C. for 1 hour.

Under a pressure of about 750 psig, the catalyst is then contacted with a $H_2/CO$ reactant gas at a ratio of 1/1 and at a total flow rate of 1.0 SLPM (Standard Liters per Minute). The reactor was then slowly heated from room temperature (20° C.) to 225° C. (over 1.5 hours), then the temperature was raised to 250° C. over 0.5 hours and finally maintained at 250° C. for 3.5 hours.

The liquid products were collected by condensation at 0° C. and were then weighed and analyzed by gas chromatography. The results are shown in Table I.

The above catalysts were run again under identical conditions except that the reaction temperature was 300° C. The results are shown in Table I.

The surface areas of the above prepared catalysts were measured by nitrogen adsorption at 77° K. The respective surface areas are shown in Table I.

As shown in Table I, high amounts of alcohols are produced from the reaction of $H_2/CO$ over the inventive catalyst. More particularly, the inventive catalyst is highly selective to $C_1$ to $C_4$ alcohols and is highly active at temperatures below about 300° C. which is more desirable for the production of methanol.

TABLE I

Alcohol Synthesis Using Catalysts Derived From Intermetallic Compounds

| Example | Catalyst | Temperature °C. | Total CO** Conversion | % Selectivity to Alcohols* $C_0$ | $C_2$ | $C_3$ | $C_4$ | Catalyst Surface Area |
|---|---|---|---|---|---|---|---|---|
| 1 | $Cu_2ThPdO_x$ | 250 | 12.17 | 81.76 | 1.45 | 0.22 | 0.30 | 21.5 |
|   |   | 300 | 10.05 | 29.46 | 0.71 | 0.46 | 1.48 | 21.5 |
| 2 | $Cu_2ThCeO_x$ | 250 | 19.99 | 89.19 | 1.24 | 0.23 | 0.19 | 34.7 |
|   |   | 300 | 15.39 | 56.40 | 0.99 | 0.81 | 2.24 | 34.7 |
| 3 | $Cu_2ThZnO_x$ | 250 | 16.74 | 94.21 | 2.53 | 0.53 | 0.00 | 51.3 |
|   |   | 300 | 14.54 | 57.26 | 2.64 | 1.56 | 4.77 | 51.3 |
| 4 | $Cu_2CeCrO_x$ | 250 | 15.16 | 88.30 | 2.23 | 0.61 | 0.49 | 18.6 |
|   |   | 300 | 12.73 | 56.60 | 1.69 | 1.50 | 2.84 | 18.6 |
| 5 | $Cu_2CeZnO_x$ | 250 | 10.19 | 91.26 | 2.51 | 0.73 | 0.54 | 9.1 |
|   |   | 300 | 10.94 | 76.36 | 2.48 | 1.81 | 4.47 | 9.1 |

*selectivity = (moles C in product/moles CO converted to all products) × 100

**conversion = $\frac{\text{moles CO reacted to all products}}{\text{moles CO fed}} \times 100$

We claim:

1. A process for preparing a catalyst containing at least three metals which process comprises at least partially oxidizing an intermetallic compound containing two or more of said metals by heating with a solution of a metal-containing oxidizing agent whereby the metal of the metal-containing oxidizing agent is incorporated into said intermetallic compound to thereby form said catalyst.

2. A process as claimed in claim 1 wherein the metal-containing oxidizing agent is in solution in water.

3. A process as claimed in claim 1 wherein the catalyst is separated from the solution, dried and calcined at a temperature from 250° to 500° C.

4. The process of claim 1 wherein said intermetallic compound contains at least one metal selected from La, Th, Ce, U, Cu, Rh, Ru, Ir, Fe, Co, Pd, Pt, with a metal oxidizing agent wherein said agent is incorporated into said compound thereby from said catalyst.

5. The process of claim 1 wherein said intermetallic compound contains at least one metal selected from Th, Ce, Cu, Pd and Cr.

6. The process of claim 5 wherein said intermetallic compound contains copper.

7. The process of claim 5 wherein said metal is present in an amount of more than 10 percent by weight.

8. The process of claim 1 wherein said metal oxidizing agent is selected from Zn, Cr, Co, Mn, Ce, V, Pd, Cu, Ag, Fe, U, Rh, Ru, Os, Ir, Ni and Th.

9. The process of claim 1 wherein said metal oxidizing agent is selected from Zn, Cr, Ce and Pd.

* * * * *